(12) United States Patent
Kuster et al.

(10) Patent No.: US 10,145,796 B2
(45) Date of Patent: Dec. 4, 2018

(54) ILLUMINATION FILTER FOR AN ILLUMINATION FILTER SYSTEM OF A SURGICAL MULTISPECTRAL FLUORESCENCE MICROSCOPE HAVING A SPATIAL FILTER PATTERN

(71) Applicant: LEICA INSTRUMENTS (SINGAPORE) PTE. LTD., Singapore (SG)

(72) Inventors: Manfred Kuster, Widnau (CH); George Themelis, Lindau (DE)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 0 days.

(21) Appl. No.: 15/424,817

(22) Filed: Feb. 4, 2017

(65) Prior Publication Data
US 2017/0234796 A1   Aug. 17, 2017

(30) Foreign Application Priority Data
Feb. 15, 2016  (EP) ..................................... 16155624

(51) Int. Cl.
  *G01N 21/64* (2006.01)
  *A61B 1/04* (2006.01)
  (Continued)

(52) U.S. Cl.
  CPC ......... *G01N 21/6458* (2013.01); *A61B 1/043* (2013.01); *A61B 1/0646* (2013.01);
  (Continued)

(58) Field of Classification Search
  CPC .......... G01N 21/6458; G01N 21/6456; G01N 21/64; G01N 2201/068; G02B 21/16; G02B 21/06
  (Continued)

(56) References Cited

U.S. PATENT DOCUMENTS 6,099,466 A  *  8/2000  Sano ................... A61B 1/00186
                                                            600/109
6,747,280 B1     6/2004  Weiss
                (Continued)

FOREIGN PATENT DOCUMENTS

CH       526789      8/1972
EP      1158330     11/2001
        (Continued)

OTHER PUBLICATIONS

De Grand, et al., An Operational Near-Infrared Fluorrescence Imaging System Prototype for Large Animal Surgery, Technology in Cancer Research & Treatment, vol. 2, No. 6, 10 pages Dec 1, 2003.
(Continued)

*Primary Examiner* — William R Alexander
(74) *Attorney, Agent, or Firm* — Hodgson Russ LLP

(57) ABSTRACT

The invention relates to an illumination filter (36, 44) for an illumination filter system (2) for medical imaging, in particular multispectral fluorescence imaging, as performed e.g. in a microscope (1) or endoscope, in particular a multispectral fluorescence microscope. The present invention provides an illumination filter for medical imaging, in particular a multispectral fluorescence imaging, that is capable of capturing simultaneously more than one fluorescence signal, and allow a homogeneous illumination for obtaining different images from the object illuminated by comprising a spatial filter pattern (43) masking a defined filtering fraction of a first illumination path (47) on the filter and masking a defined filtering fraction of a second illumination path (48, 49, 50) on the filter, wherein the filtering fraction of the first and the second illumination paths (47, 48, 49, 50) are different. The invention further relates to an illumination filter system (2) for medical imaging, in particular multispectral fluorescence imaging, as performed e.g. in a microscope (1) or endoscope, in particular a multispectral fluo-
(Continued)

rescence microscope, comprising such illumination filter (36, 44).

14 Claims, 8 Drawing Sheets

(51) Int. Cl.
    *A61B 1/06*     (2006.01)
    *G02B 21/06*     (2006.01)
    *G02B 21/16*     (2006.01)
    *F21V 9/40*     (2018.01)
    *G02B 26/00*     (2006.01)
    *G02B 26/02*     (2006.01)
    *G02B 5/20*     (2006.01)

(52) U.S. Cl.
    CPC ............. *G01N 21/64* (2013.01); *G02B 21/06* (2013.01); *G02B 21/16* (2013.01); *F21V 9/40* (2018.02); *G01N 2021/6471* (2013.01); *G01N 2201/068* (2013.01); *G02B 5/201* (2013.01); *G02B 26/008* (2013.01); *G02B 26/023* (2013.01)

(58) Field of Classification Search
    USPC .................................. 359/350, 339, 888, 891
    See application file for complete search history.

(56) References Cited

U.S. PATENT DOCUMENTS

| | | | | |
|---|---|---|---|---|
| 7,330,749 | B1* | 2/2008 | Bhunachet | A61B 1/042 |
| | | | | 600/109 |
| 7,924,517 | B2* | 4/2011 | Ambar | G02B 27/46 |
| | | | | 359/891 |
| 9,958,388 | B2* | 5/2018 | Imagawa | G01N 21/64 |
| 2001/0042837 | A1* | 11/2001 | Hoffmann | G02B 21/0032 |
| | | | | 250/458.1 |
| 2003/0011910 | A1 | 1/2003 | Weiss | |
| 2009/0225410 | A1* | 9/2009 | Fey | G02B 21/16 |
| | | | | 359/385 |
| 2010/0110538 | A1 | 5/2010 | Steffen et al. | |
| 2010/0182712 | A1* | 7/2010 | Chinnock | G01J 1/24 |
| | | | | 359/890 |
| 2011/0279901 | A1* | 11/2011 | Watanabe | G02B 5/285 |
| | | | | 359/589 |
| 2012/0248333 | A1 | 10/2012 | Fallert et al. | |
| 2014/0027653 | A1 | 1/2014 | Mori et al. | |
| 2015/0083932 | A1* | 3/2015 | Rizo | A61B 5/0071 |
| | | | | 250/458.1 |
| 2015/0346098 | A1 | 12/2015 | Hauger et al. | |

FOREIGN PATENT DOCUMENTS

| | | |
|---|---|---|
| GB | 2075698 | 11/1981 |
| JP | 2012098271 A | 5/2012 |

OTHER PUBLICATIONS

Sato, et al., Development of a new high-resolution intraoperative imaging system (dual-image videoangiography, DIVA) to simultaneously visualize light ande near-infrared fluorescence images of indocyanine green angiography, Acta Neurochirurgica, vol. 157, No. 8, pp. 1295-1301 Jul. 8, 2015.

Thorlabs, Rectangular Step Variable Metallic Neutral Density Filters, available at URL:https://www.thorlabs.com/thorcat/12300/NDL-25S-4-AutoCADPDF.pdf Dec. 31, 2010.

* cited by examiner

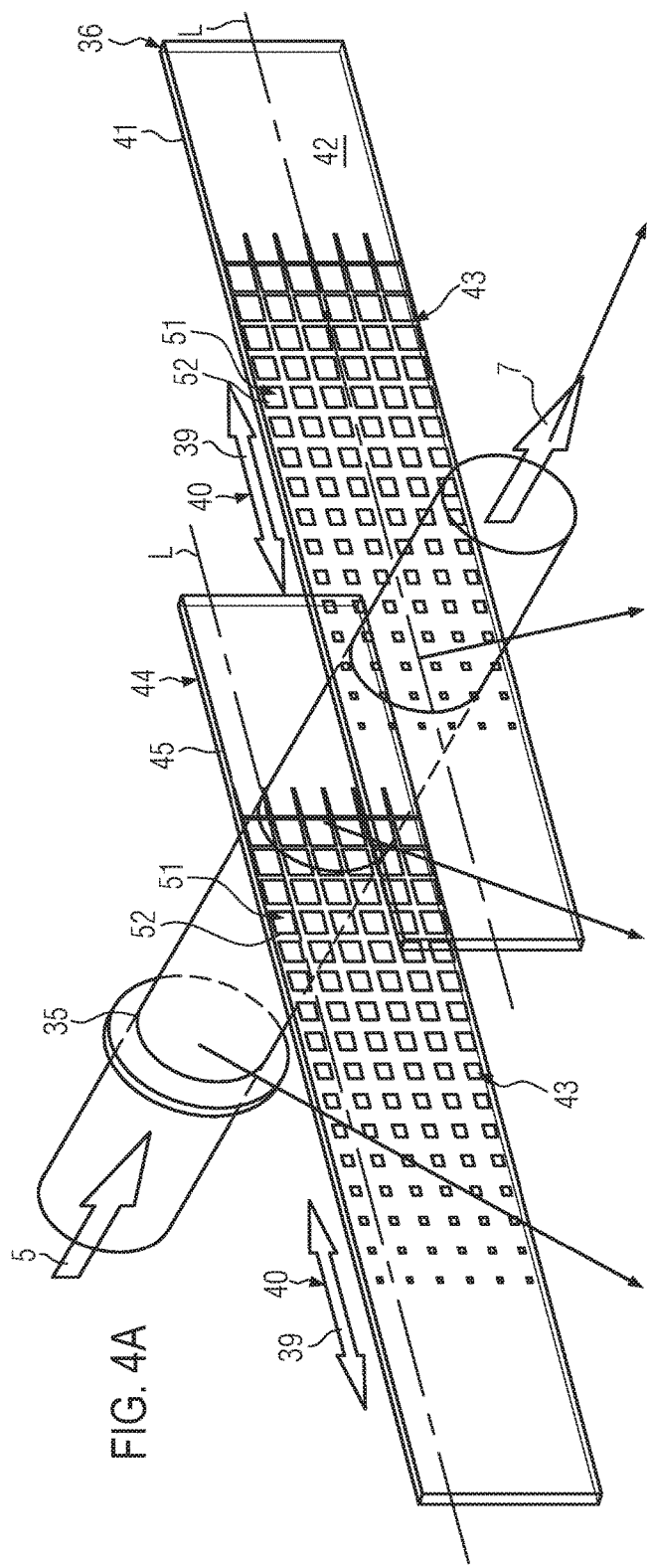
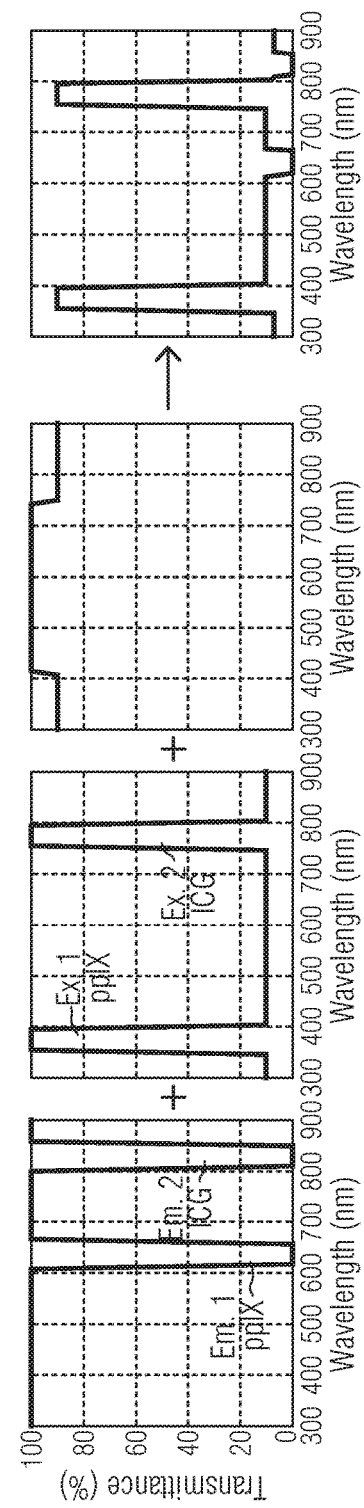
FIG. 4A
FIG. 4B

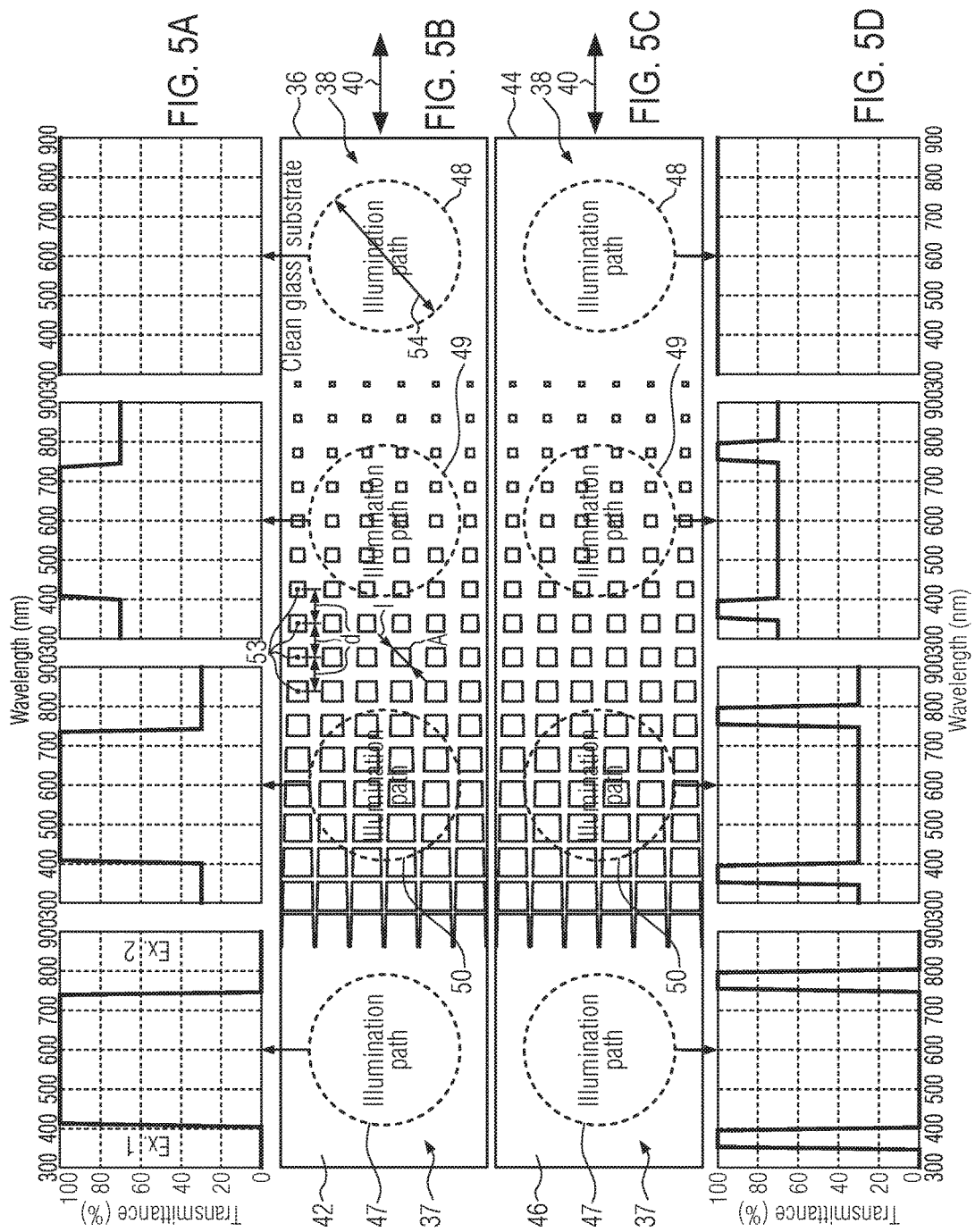

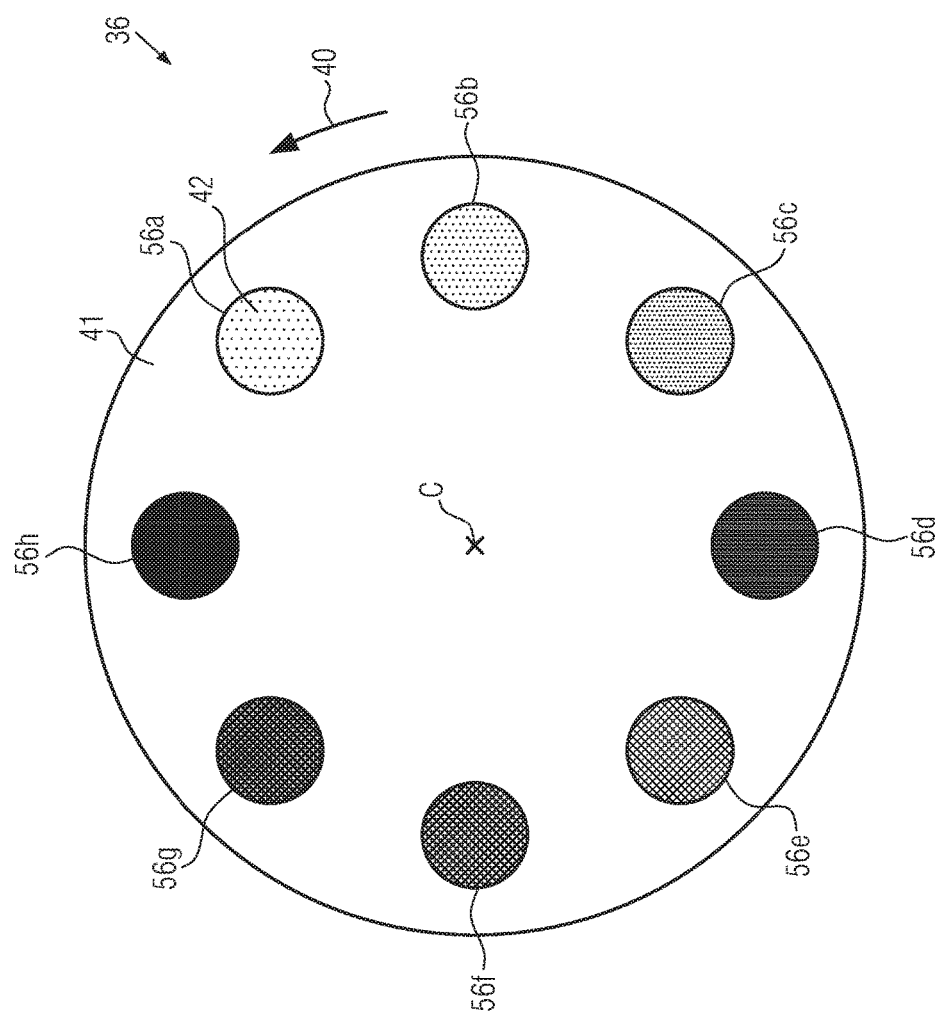

ILLUMINATION FILTER FOR AN ILLUMINATION FILTER SYSTEM OF A SURGICAL MULTISPECTRAL FLUORESCENCE MICROSCOPE HAVING A SPATIAL FILTER PATTERN

CROSS REFERENCE TO RELATED APPLICATIONS

This application claims priority of European patent application number 16155624.6 filed Feb. 15, 2016, the entire disclosure of which is incorporated by reference herein.

FIELD OF THE INVENTION

The present invention relates to an illumination filter for an illumination filter system for medical imaging, in particular multispectral fluorescence imaging, as performed e.g. in a microscope or endoscope, such as a surgical microscope, in particular a surgical multispectral fluorescence microscope.

The present invention further relates to an illumination filter system for medical imaging, in particular multispectral fluorescence imaging, as performed e.g. in a microscope or endoscope, such as a surgical microscope, in particular a surgical multispectral fluorescence microscope.

BACKGROUND OF THE INVENTION

Microscope systems for imaging a color image of reflected visible light and a fluorescence image from an object simultaneously are known from e.g. De Grand and Frangioni, "*Operational near-infrared fluorescence imaging system prototype for large animal surgery*", Technology in Cancer Research & Treatment, Volume 2, No. 6, December 2003, pp 1-10, or from Sato et al. "*Development of a new high-resolution intraoperative imaging system (dual-image videoangiography, DIVA) to simultaneously visualize light and near-infrared fluorescence images of indocyanine green angiography*", Acta Neurochirurgica (2015) Volume 157, pp 1295-1301. These systems require two light sources, an illumination filter system for each light source as well as an observation system for capturing the image of visible reflected light as well as fluorescence light emitted from the object. Using two light sources is equipment intensive, costly and requires bulky instrumentation. Further, these systems show inhomogeneities in illumination due to the two light sources used, and only one fluorophore can be used at a time with these systems.

SUMMARY OF THE INVENTION

It is therefore the object of the present invention to provide an illumination filter and illumination filter systems for medical imaging, in particular multispectral fluorescence imaging, as performed e.g. in a microscope or endoscope, in particular a surgical multispectral fluorescence microscope, that are capable of capturing simultaneously more than one fluorescence signal, and allow a homogeneous illumination for obtaining different images from the object illuminated.

This object is achieved for the illumination filter as initially mentioned in that the filter comprises a spatial filter pattern masking a defined filtering fraction of a first illumination path on the filter and masking a defined filtering fraction of a second illumination path on the filter, wherein the filtering fraction of the first illumination path is different from the filtering fraction of the second illumination path.

For the illumination filter system mentioned at the beginning, this object is solved by comprising at least one illumination filter system according to the present invention.

The inventive illumination filter allows an intensity adjustment in illumination systems due to the spatial filter pattern. By switching from the first to the second illumination path and vice versa, the transmittance of the illumination filter may be set to the intended value. The transmittance is determined by the filtering fraction of the spatial filter pattern masking the respective illumination path. An "illumination path" is a distinct area of the filter that is arranged in the light path, i.e. is in optical communication, with a light source. In other words, an illumination path is that part of the filter through which light passes in operation. A "filtering fraction" is that part of an illumination path which filters the light from the light source, relating to the whole illumination path. For example, a filtering fraction of 50 means that half the of light passing through the illumination path is filtered, while the other half of light passes unfiltered. By masking different filtering fractions of the first illumination path and of the second illumination path, the illumination filter may adjust the degree of attenuation, or in other words the degree of filtering efficiency or the degree of transmittance of light having a certain range to be filtered may be adjusted.

The solutions according to the invention can be improved by the following advantageous features, which are independent of one another and can be combined independently. Further, all features described with respect to the inventive apparatus can be used and accordingly applied in the inventive microscopying method.

In one embodiment, the illumination filter may comprise a filter coating applied as the spatial filter pattern on the substrate, said coating defining the filtering fraction of the first and the second illumination path on the substrate. The coating may cover a defined portion of the illumination path, while leaving other areas of the illumination path uncovered in order to obtain a filtering fraction of below 100% and above 0%, or the illumination path may be completely coated, however, the coating comprises a certain concentration of a filtering compound filtering and thus defining the distinct filtering fraction of the light passing through the illumination path. Alternatively, a filtering substance, i.e. a compound absorbing radiation having a certain wavelength, may be embedded within the substrate in a certain amount/concentration defining the filtering fraction of the first and the second illumination path of the substrate.

The spatial filter pattern may be a band-stop filter pattern or a band-pass filter pattern. The band-stop filter pattern may comprise a filtering fraction blocking fluorescence excitation bands. The band-stop filter may be adapted to transmit all wave lengths of visible light except the quenched fluorescence excitation bands in the visible spectrum. This way, the degree of attenuation of the fluorescence excitation bands may be adjusted because the transmittance thereof directly correlates with the filtering fraction in the respective illumination path. In other words, the filtering fraction, i.e. those areas of the illumination path which filters, e.g. because it is coated with a filter coating or because filtering compounds are embedded there, always quenches, i.e. completely blocks light of a fluorescence excitation band. The filtering fraction then determines the total amount of light of a fluorescence excitation band. For example, if the spatial filter pattern masks a filtering fraction of 90% of a first illumination path, 90% of light having a fluorescence excitation band will be quenched. If another illumination path comprises a filtering faction of 30%, only 30% of the light having a fluorescence excitation band will be quenched in said illumination path. A band-stop filter pattern thus allows adjusting the intensity of light in a fluorescence excitation band transmitted by the adjustable illumination filter of the present invention.

For example, the inventive illumination filter system may be adapted for multispectral imaging, in particular multispectral fluorescence imaging. The illumination filter system may be adapted for a multispectral fluorescence microscope. Such multispectral fluorescence microscope acquires simultaneously at least two, preferably three or more images, such as for example two or more fluorescence signals, or one fluorescence signal, in particular a signal of fluorescence band in a visible spectrum, as well as a visible color reflectance image, or a visible reflectance image as well as at least two fluorescence signals. The preceding list is not exhaustive and the illumination filter system can be easily adapted to the required multispectral image to be acquired.

Depending on the number of fluorescence signals to be detected, the band-stop filter may be a dual-band-stop filter or a triple-band-stop filter if two or three, respectively, fluorescence signals are to be detected.

A band-pass pattern allows an adjustment of attenuation/transmittance of light outside the pass-band frequency, i.e. attenuates or quenches the light outside the range of wavelengths that can pass through the band-pass filter. The band-pass filter providing the band-pass filter pattern may be adapted to transmit light of the fluorescence excitation band only. This way, the band-pass filter pattern may e.g. be used to adjust the intensity of white light passing the illumination filter. The filtering fraction that is masked by the band-pass filter in an illumination path determines how much light outside the pass-band of the band-pass filter pattern passes through.

The band-stop filter pattern or the band-pass filter pattern may be a band-stop filter coating applied as the spatial filter pattern on a substrate. Likewise, a band-stop filter compound or a band-pass filter compound may be embedded in the substrate in a predetermined concentration corresponding to the intended filtering fraction masking the corresponding illumination path.

The illumination filter can thus adjust e.g. the degree of attenuation of the fluorescence excitation bands. Adjusting the degree of attenuation allows an adjustment of the intensity of the excitation light relative to the intensity of white (or visible) light providing a homogenous illumination of the object and improving the quality of the signals/image captured in a microscope using the inventive illumination filter system.

In a further embodiment, the illumination filter may comprise a filtering fraction masking 100% of a first illumination path and a filtering fraction of less than 100% and preferably over 0% of a second illumination path on the substrate.

The expression "illumination path" defines a specific area the illumination filter through which light emitted from the light source passes. In other words, the illumination path is that section of the filter which is in optical communication with light source. Optical communication means that illumination light is directed onto and passing through the filter. In other words, the expression "optical communication" means that the respective elements are arranged along the same light path. If the filter is displaced with respect to a light source, the illumination path on the filter likewise changes. In this respect, it is to be noted that different illumination paths on the filter may partially overlap. Thus, a plurality of different illumination paths may be provided on a single illumination filter.

The filter substrate may essentially transmit all illumination light, e.g. the substrate may be a glass, i.e. the coverage substrate. The ratio of coated versus uncoated areas within a specific illumination path may then determine the filtering fraction, i.e. the percentage of attenuation for said illumination path.

The band-stop filter coating may attenuate always 100% of the respective fluorescence excitation band(s). Thus, the percentage of coating within a specific illumination path determines the degree of attenuation of fluorescence excitation bands in said illumination path.

The band-pass filter may always have 100% transmittance for the respective fluorescence excitation bands, while quenching, i.e. eliminating essentially all other wavelengths. Thus, the filtering fraction in a band-pass filter pattern determines the degree of attenuation of light having a wavelength outside the fluorescence excitation wavelength. Because of this, for example the degree of attenuation of the intensity of white light may be adjusted. The intensity adjustment of the present invention allows to use an illumination system in a microscope having one light source only, such as for example a light source emitting illumination light having a wavelength of e.g. 300-900 nm, preferably of 380-800 nm.

Applying a filtering pattern may likewise allow adjusting the intensity of different fluorescence excitation bands with respect to each other. For example, a filter may be a dual band-pass filter for a first and a second fluorescence excitation band. The illumination filter may comprise a spatial single band-pass filter pattern, e.g. a filter coating material having 100% transmittance for the second fluorescence excitation band only, said filter coating material being applied in a spatial filter pattern as described above and below. This way, the relative intensities of the light in the first fluorescence excitation band may be adjusted relative to the intensity of the light in the second fluorescence excitation band.

According to a further embodiment, the spatial filter pattern may extend over a plurality of illumination paths provided on the filter and the masked filtering pattern is different in each illumination path. The masking of the filtering fraction, which can also be termed coverage of the filtering material, may either change stepwise or gradually from one illumination path to another.

The plurality of illumination paths may be arranged along an axis of the illumination filter. Along this axis, also called axis of movement, the illumination filter may be configured to be moved from a first operation position, in which the first illumination path is in optical communication with a light source, to a second operation position, in which the second illumination path is in optical communication with the light source, in an embodiment of the illumination filter system. For example, the substrate of the filter may be a slide, i.e. a glass plate having a substantially rectangular, preferably elongated shape. This slide may be moved along a linear axis of movement, the longitudinal axis of the slide. In another embodiment, the substrate may be disc-shaped, which disc may have a rotational axis of movement. The disc may be rotated about its center in order to shift from the first into the second operation position. Other embodiments are likewise possible. For example, the substrate may have a rectangular shape with different, distinct illumination paths that do not overlap and which may be individually placed in the illumination light path when displacing the substrate accordingly.

In one embodiment, the spatial pattern may comprise a plurality of filter patches, e.g. spots in which the substrates are coated, or distinct sections where a filtering material is embedded in the substrate. The center of adjacent patches is preferably spaced essentially equidistant from each other. In order to achieve a different coverage, i.e. a different filtering fraction in a specific illumination path, the area of patches may vary. The center of the patch may be the geometrical center, e.g. the center of the circle where the diameters cross each other or the center of a different shape, such as a square, rectangle, rhombus, or parallelogram, where the diagonals intersect. The area of a patch is the surface of the substrate covered by said patch.

In one embodiment, the filtering patches may be filter squares. The diagonal length of the squares may vary, preferably along the axis of the illumination filter. This way, it is possible to obtain a spatial filter pattern having a gradually dropping coverage along the axis of the illumination filter.

For example, in case of the substrate being a slide, a constant number of coating patches/coating squares may be applied in both, the longitudinal as well as the width direction of the slide. In the longitudinal and the width direction, the distance between the adjacent centers of the squares may be the same. In the width direction, all adjacent squares may have the same diagonal length, hence the same area. In the longitudinal direction, the diagonal length and thus the area of the squares may successively increase.

The distance between the centers of patches as well as the length of the patches/squares are preferably significantly smaller than the area of the illumination paths. Significantly smaller means that the distance/length of patches is smaller by an order of 10.

The illumination filter system of the present invention allows to adjust the intensities of different wavelengths of illumination light such as the intensities of fluorescence excitation bands and the white light intensity. The present invention allows adjusting these intensities individually, i.e. adjust the intensity of white light with respect to a first fluorescence excitation band or allows to adjust the intensity of the white light and the first fluorescence excitation band with respect to the second fluorescence excitation band. This improves to simultaneously capture the image of visible light reflected from the object as well as the signals of the fluorescence emission bands.

According to one embodiment of the illumination filter system, the illumination filter may, as already discussed above, be configured to be moved from a first operation position, in which the first illumination path is in optical communication with the light source, to a second operation position, in which the second illumination path is in optical communication with the light source. In particular, the illumination filter is configured to be moved along the axis of the illumination filter, the axis of movement. For example a disc-shaped illumination filter may be rotated about its center of rotation and an illumination filter having a slide as a substrate, may be moved along the longitudinal axis of the slide.

According to a further embodiment of the illumination filter system, the system may comprise a first illumination filter having a spatial band-stop filter pattern and a second illumination filter having a spatial band-pass filter pattern. Each of the first and second illumination filter may be configured to be moved from a first operation position to a second operation position, preferably along the axis of the illumination filter. This way, the amount of white light as well as the amount of fluorescence excitation bands may be individually adjusted.

In a further embodiment, the illumination filter system may further comprise a blocking filter adapted to quench light of a fluorescence emission band. The blocking filter may quench all fluorescence emission bands. For example, if three fluorescence signals are to be captured, the blocking filter may be a triple-band-stop filter quenching the corresponding three fluorescence bands. It is also possible to use multiple single-band-stop filters arranged in series, i.e. in optical communication one after another, as a blocking filter. The blocking filter may be adapted to transmit the fluorescence excitation bands and visible lights, except for the quenched fluorescence emission bands falling into the spectrum of visible lights. The blocking filter may be a notch filter, for example a dual-notch filter in case two fluorescence signals are to be captured simultaneously, or a triple-notch filter in case three fluorescence signals are to be capture simultaneously and so on. The blocking filter may be arranged in optical communication with the illumination filter(s) in a further embodiment of the illumination filter system.

The present invention further relates to a medical imaging apparatus, such as a microscope or endoscope, or a surgical microscope, in particular a multispectral fluorescence microscope comprising an illumination filter or an illumination filter system described above.

In the following, the invention is described in greater detail in exemplary embodiments with reference to the accompanying figures. The various features in the embodiments may be freely combined as is explained above. If, for a particular application, the advantage which is realized by a particular feature is not needed, this feature can be omitted.

BRIEF DESCRIPTION OF THE DRAWING VIEWS

In the drawings, the same reference numeral is used for elements which correspond to each other with respect to their design and/or their function.

In the drawings:

FIG. 4A shows an illumination filter system according to a second embodiment comprising an illumination filter in another exemplary embodiment;

FIG. 4B shows the spectral characteristics of the individual illumination filters encompassed by the illumination filter system as shown in FIG. 4A as well as the spectra characteristics of the whole illumination filter system;

FIG. 5A shows the spectral characteristics of the illumination filter of FIG. 5B in the respective illumination path;

FIG. 5B shows an illumination filter in an exemplary embodiment;

FIG. 5C shows another illumination filter of another embodiment;

FIG. 5D shows the spectral characteristics of the illumination filter of FIG. 5C in the respective illumination path;

FIG. 7 shows an illumination filter according a further embodiment having a disc-shaped substrate.

DETAILED DESCRIPTION OF THE INVENTION

Figure 1:
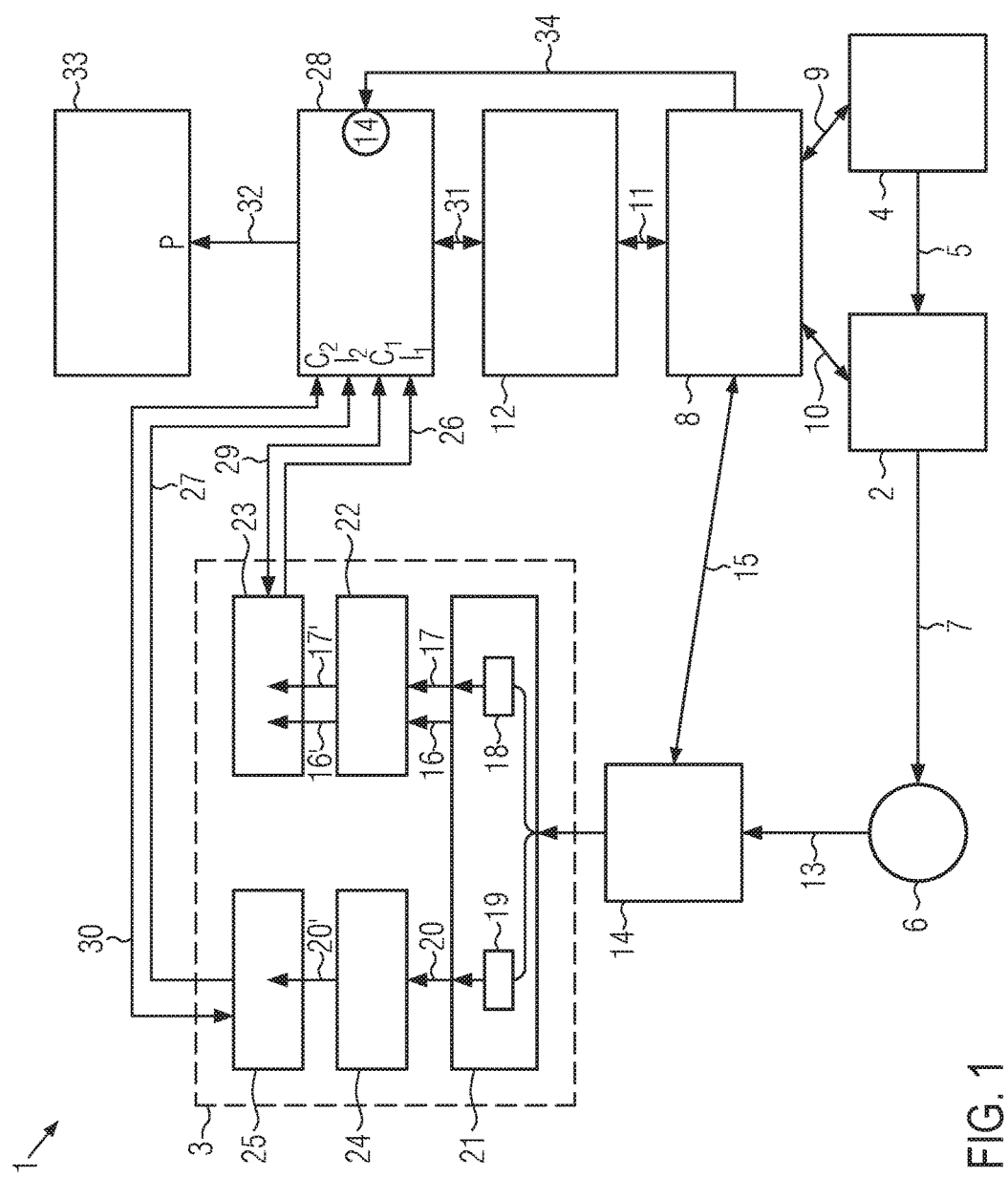
FIG. 1 shows a schematic block diagram of a medical imaging apparatus in which the illumination filter or the illumination filter system of the invention can be applied.

First, the design and function of a medical imaging apparatus 1, such as a microscope 1 or endoscope comprising an illumination filter system 2 as well as an observation system 3 is explained with reference to FIG. 1. The microscope 1 comprises a light source 4 that emits an illumination light 5 onto an object 6 to be observed. The illumination filter system 2 is in optical communication with the light source 4 as well as the object 6, that is, the illumination system 2 is in the light path of the illumination light 5 from the light source 4 to the object 6.

The illumination filter system 2 filters and spectrally modifies the illumination light 5. It adjusts the intensity of specific portions within the illumination light 5 relative to each other using an illumination filter of the present invention, as will be explained in more detail below with respect to preferred embodiments of the illumination filters and the illumination filter system 2 of the present invention. Thus, spectrally modified illumination light 7 exits the illumination filter system 2 and is directed onto the object 6. The spectrally modified illumination light 7 is specifically adapted in order to improve a multi-spectral fluorescence microscopying method. In the shown embodiment, the spectrally modified illumination light 7, provided by the illumination filter system 2, is adapted in order to capture a reflected visible image as well as two fluorescence signals simultaneously, which will also be described in more detail below.

The light source 4 as well as the illumination filter system 2 are both regulated by a controller 8. The controller 8 is connected with the light source 4 via a bi-directional signal line 9, via which the controller 8 may regulate, for example, the intensity of the illumination light 5 or, in case of a light unit having two different light sources, selects the respective light source for emitting the illumination light 5. Via another bi-directional signal line 10, the controller 8 also regulates the illumination filter system 2, e.g. by setting the filters for adjusting the degree of attenuation of certain filters in order to adjust the ratio of light intensities of certain spectral bands included in the spectrally modified illumination light 7. Using bi-directional signal lines 9, 10 allows a loop-control of the settings of the light source 4 and the filter system 2.

The controller 8 itself is coupled via a further bi-directional signal line 11 with a controller interface 12 for inputting settings of the microscope.

A light image 13 is sent from the object 6 to the observation system 3 at defined microscope settings 14. In FIG. 1, the microscope observation settings 14, such as the working distance, magnification, elements used the observation system 3 are represented as a box. The controller 8 may adjust the observation parameters of the microscope via a further signal line 15. The light image 13 sent from object 6 to observation system 3, is split into a first light portion 16, 17 along the first light path 18 and the second light portion 20 along a second light path 19 in a beam splitter 21 of the observation system 3. The first light portion 16, 17 comprises two fluorescence emission bands. The second light portion comprises reflected visible light (VISR), i.e. the visible light reflected from the object. The first light portion 16, 17 passes a band-pass filter 22. The first emission band and the second fluorescence emission band of the first light portion 16', 17' exiting the band-pass filter 22 are captured by the fluorescence sensor 23. The fluorescence sensor 23 may for example be a fluorescence camera, for example, an NIR camera if the fluorescent emission bands are in the near infrared range.

The second light portion 20 passes through the band-stop filter 24. The reflected visible light of the second light portion 20' exiting the band-stop filter 24 is captured by a second sensor 25. The second sensor 25 may be a visible camera such as for example a charge coupled device (CCD).

The first sensor 23, sends, via a signal line 26 a first image read-out $I_1$ comprising information on the captured fluorescence emission bands to a processing unit 28. A second image readout $I_2$ is sent via a signal line 27 from a second sensor 25 to the processing unit 28. The image readout $I_2$ contains the image data of the reflected visible light 20' captured by the sensor 25.

The processing unit 28 is further connected to each of the sensor 23 and the sensor 25 by a bi-directional signal lines 29 and 30, respectively. Via these bi-directional signal lines 29, 30, the processing unit 28 controls the sensors 23 and 25 and reads out the settings of said sensors 23, 25 allowing a loop-control of the sensors 23, 25 by the processing unit 28. The processing unit 28 itself may receive the settings from a user of the microscope by inputting the corresponding parameters into the controller interface 12 and sending the settings via a signal line 31.

The processing unit 28 may process the image readouts $I_1$ and $I_2$. In a preferred embodiment, a pseudo-image P may be generated by the processing unit 28 and sent from the processing unit 28 via signal line 32 to a display device 33, such as for example, a monitor. Even though it is not shown in FIG. 1, the pseudo-image P may be stored in a documentation system. The pseudo-image P may be a merger of the image readout $I_1$ from the fluorescence (FL) sensor 23 and the VISR image readout $I_2$ from the visible camera 25. It is to be noted that the merged pseudo-image P is not merely an overlay of the image readouts $I_1$ and $I_2$. The pseudo-image P does not obscure any image readout information (which would be the case by overlaying the two image readouts $I_1$ and $I_2$), but rather presents the fluorescence image readout within the VISR image readout $I_2$ in a natural way, resembling the injection of a bright dye. The pseudo-image P may be generated in real time allowing the user of the microscope 1 to capture a combination of the white light image and fluorescence light signals in one merged image.

In order to improve the quality of the pseudo-image P, the image readouts $I_1$ and $I_2$ may be homogenized. The homogenization may correct inhomogeneities in illumination and vignetting of the image optics which would otherwise result in an uneven brightness across the field of view as the periphery of the field of view may be significantly darker at the periphery than in the center. Further, the homogenized image readouts $I_1$ and $I_2$ may be aligned with each other before merging. For example, a spatial correction transformation may be performed to correct alignment errors in the relative position of the two sensors 23 and 25 and digital filters may be applied taking into consideration translation, rotational and magnification mismatches between the sensors 23 and 25. Further, a threshold may be set on an image readout, in particular the image readout $I_1$ received from the fluorescence sensor 23 in order to remove a dark current from the fluorescence sensor 23, thus avoiding a false contribution in measurement of the fluorescence signals.

The controller 8 may provide the processing unit 28, via a signal line 34, with data of the microscope settings 14 that may be inputted by the user via the controller interface 12, such as for example, the working distance, magnification, as well as settings of the illumination filter system 2, the light source 1.

Figure 2A:
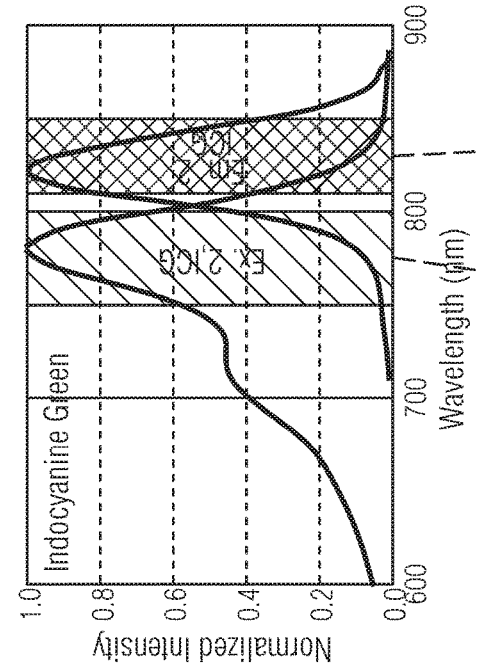
FIG. 2A shows the excitation and emission bands and spectra of 5-ALA/ppIX.
Figure 2B:
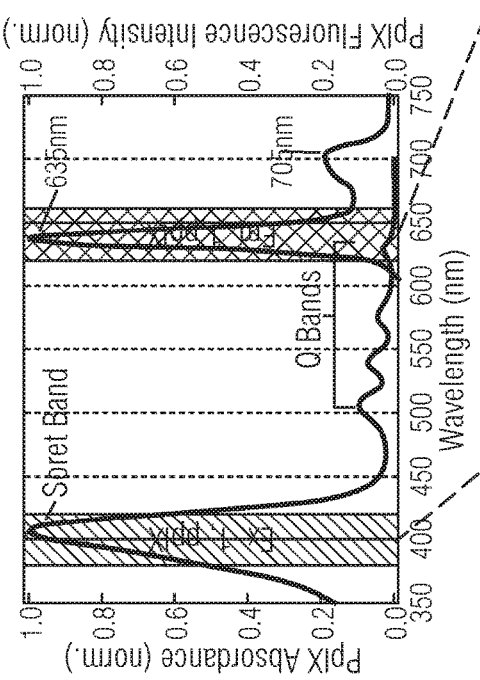
FIG. 2B shows the excitation and emission spectral and bands of Indocyanine Green (ICG)
Figure 2C:
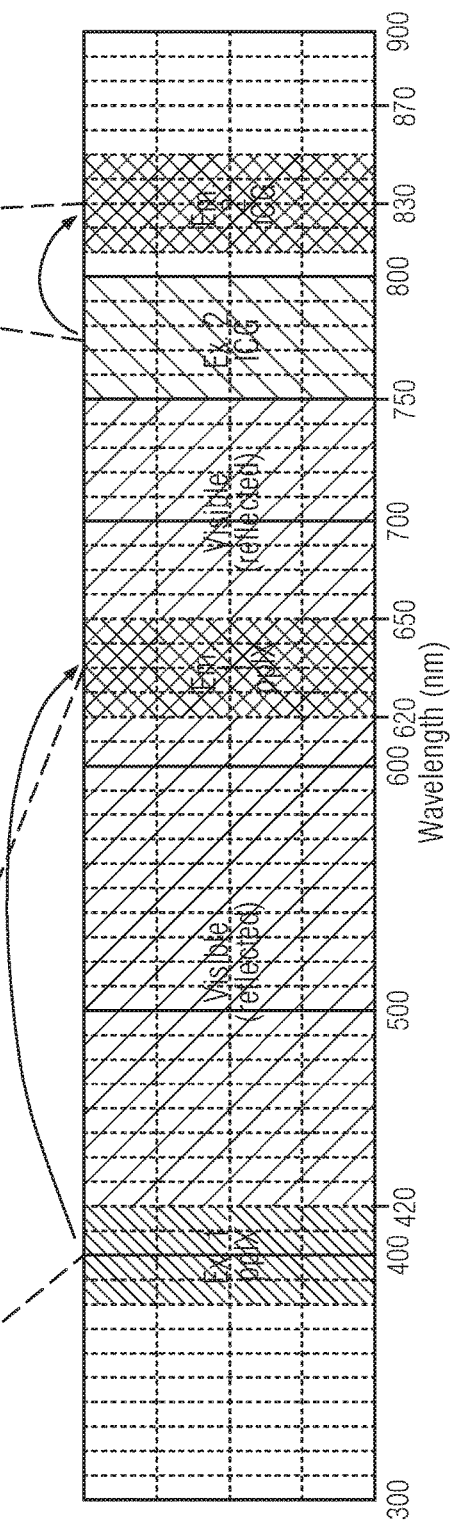
FIG. 2C shows how the spectral portions of the light used in an exemplary embodiment of the present invention is distributed over a spectrum of visible and near infrared (NIR) light.

FIGS. 2A to 2C illustrate the excitation and emission spectra of the fluorophores 5-amino levolinic acid-induced protoporphyrin IX (5-ALA/ppIX) (FIG. 2A) and indocyanine green (ICG) (FIG. 2B). Ex.1, ppIX indicates the excitation band of 5-ALA/ppIX, Em.1, ppIX indicates the fluorescence emission band of protoporphyrin IX, Ex.2, ICG indicates the fluorescent excitation band of ICG, and Em.2, ICG indicates the fluorescence emission band of ICG.

The graph of FIG. 2C shows the fluorescence excitation and emission bands as well as the visible spectrum, in particular the visible reflected (VISR) light over the wavelengths. As will be explained in more detail below, in the shown exemplary embodiments, the VISR spectrum defined in FIG. 2C is directed onto the second sensor 25, the VISR-sensor. The fluorescence emission bands Em.1, ppIX and Em.2, ICG are directed to the sensor 23, i.e. the fluorescence sensor. Thus, the spectrum of the visible reflected light indicated in FIG. 2C corresponds to the second light portion 20' in FIG. 1. The two fluorescence emission spectra Em.1, ppIX and Em.2, ICG indicated in FIG. 2C correspond to the first light portions 16' and 17', respectively.

In order to clearly distinguish the spectral bands, in particular, exclude the fluorescence excitation band of photoporphyrin IX and avoid an overlapping of the fluorescence excitation bands with the visible spectrum, in particular the visible reflected light, the illumination filter system 2 and the observation system 3 of the present invention are used, as will be explained in the following.

Figures 3A, 3B:
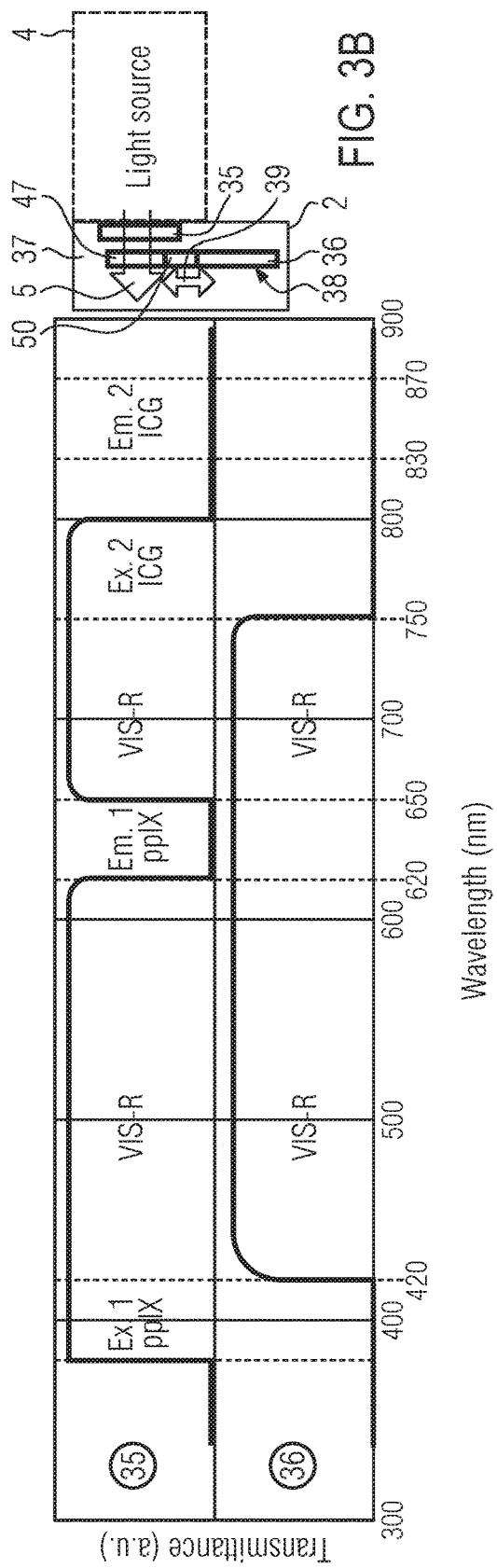
FIG. 3A shows spectral characteristics (transmittance) of an illumination filter used in an illumination filter system according to a first embodiment.
FIG. 3B shows an illumination system of a first embodiment comprising the filters having the spectral characteristics of FIG. 3A.

First, the design and function of an illumination filter system 2 according to a first embodiment is explained with reference to FIGS. 3A, 3B and 3C. FIG. 3B shows an exemplary embodiment of an illumination filter system 2 in optical communication with a light source 4. The illumination filter system 2 is arranged in the light path of the illumination light 5. The illumination filter system 2 comprises a first optical filter 35. The first optical filter 35 may be a band-stop filter. The first optical filter 35 is adapted to quench light of the fluorescence emission bands. In the shown embodiment, the fluorescence emission bands Em.1 and Em.2 for ppIX and ICG are quenched, respectively. The first optical filter 35 is always in optical communication with the light source 4, thus, the fluorescence emission bands to be detected by sensors 23 are always eliminated from the illumination light 5 by the illumination filter system 2.

The illumination filter system 2 furthermore comprises an illumination filter 36 of the present invention in an exemplary embodiment as a second optical filter 36. The second optical filter 36 may be a band-stop filter. In the following, this illumination filter 36 is referred to as the second optical filter 36. The second optical filter 36 is configured to be moved from a first operation position 37, indicated in dashed lines in FIG. 3B. In the first operation position 37, a first illumination path 47 of the second optical filter 36 is in optical communication with the light source 4 and first optical filter 35, that is, the illumination light 5 passes both the first optical filter 35 and the first illumination path 47 of the second optical filter 36 when the latter is in its first operation position 37.

The second optical filter 36 is configured to be moved from the first operation position 37 to a second operation position 38, in which another, second illumination path 48 of the second optical filter 36 is in optical communication with the light source 4 and the first optical filter 35. In the second operation position 38, the second optical filter 36 is arranged in the light path of the illumination light 5, so the illumination light 5 passes the first optical filter 35 and the second illumination path 48 of the second optical filter 36 if the latter is in its second operation position 38.

The arrow indicates the transition 39 of the second optical filter 36 from its first operation position 37 to its second operation position 38. This transition 39 may be performed, e.g. by displacing the filter 36 between its first 47 and second illumination path 48.

As can be seen in FIG. 3A, the first optical filter 35 is a band-stop filter adapted to transmit light of the fluorescence excitation bands Ex.1 of ppIX and Ex. 2, ICG as well as the whole spectrum of visible light and a portion of NIR light adjacent to the visible light, except for the quenched fluorescence emission band Em.1 of ppIX.

In one embodiment, the first optical filter 35 may be a dual-notch filter quenching the excitation bands of Em.1 ppIX and Em.2 ICG.

The illumination filter, here the second optical filter 36 is adapted to transmit the visible reflected light, except for the fluorescence excitation bands Ex.1 and Ex.2 attenuated by said second optical filter 36.

This way, the intensity of the fluorescence excitation bands may be adjusted, as will be described with more detail below referring to FIG. 3C.

The illumination filter system 2 of the present invention allows to adjust the intensity of fluorescence excitation relative to white light and/or the intensity of difference fluorescence excitation bands. Such relative intensity adjustment is useful when for example the maximum excitation power is needed, while maximum white light illumination is too bright for the use of the eyepiece of a microscope.

Figure 3C:
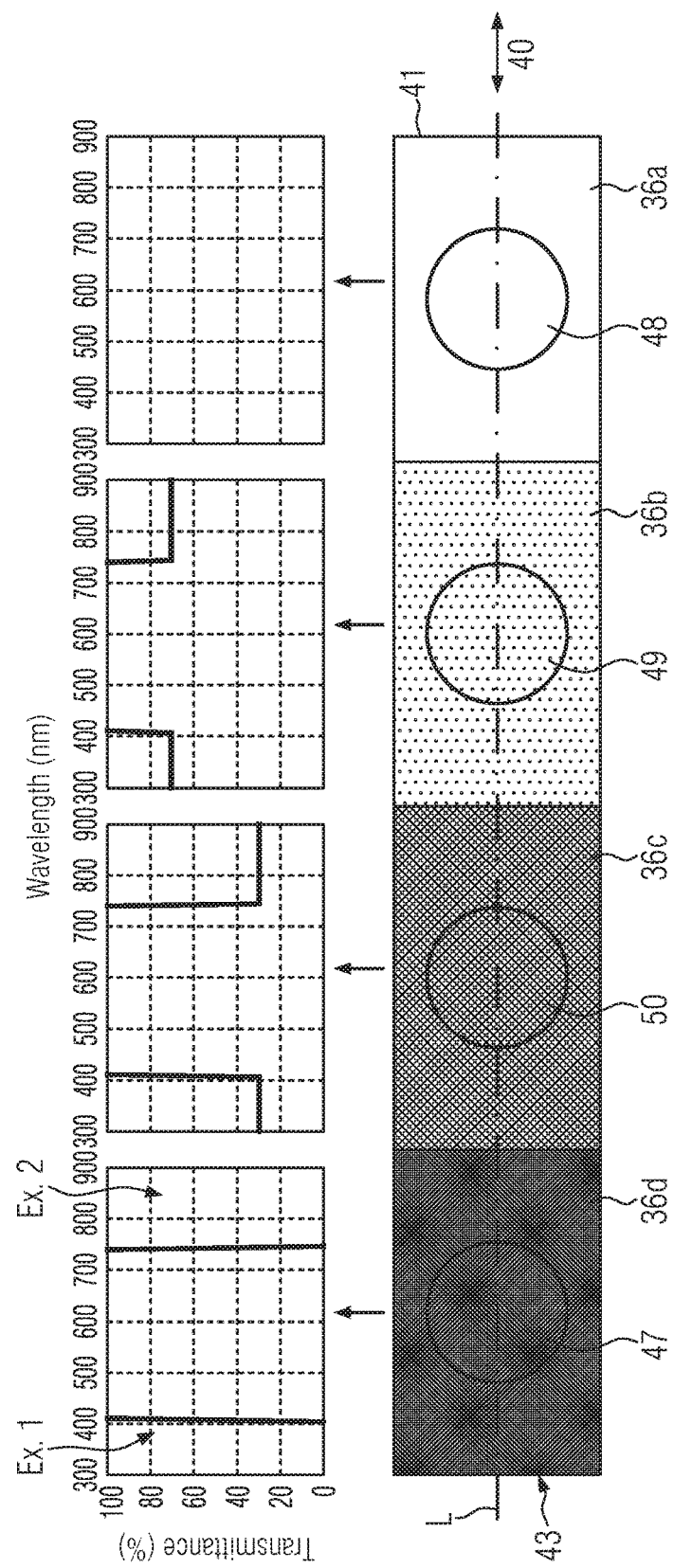
FIG. 3C shows the illumination filter of the illumination filter system of FIG. 3B in more detail together with the spectral characteristics of the illumination filter in the respective illumination path.

In FIG. 3C, the illumination filter 36 of FIG. 3B is shown in more detail. The illumination filter 36 comprises a substrate 41, which is a glass slide having a longitudinal direction L defining the axis 40 of the filter, i.e. the axis of movement. The filter 36 is divided into four sectors 36a-36d, which are adjacent to one another on the slide along the axis 40 of the slide 41. In each sector 36a-36d, the filter 36 is masked with a different defined filtering fraction for a first to fourth illumination path 47-50 of the illumination filter 36. In the shown embodiment, a filtering compound, indicated as dots, is embedded in the material of the filter substrate 41. Different concentrations of filtering material are embedded in the individual sectors 36a-36d. In sector 36a, no filtering material at all is embedded, meaning that, in the second illumination path 48, which lies in the sector 36a, the filtering fraction is zero, i.e. the adjustable illumination filter 36 has no filtering effect here. In the sector 36d, which is on the opposite end of the slide 41, relative to sector 36a, a high concentration of filtering material is embedded in the substrate 41, resulting in 100% coverage, i.e. in a filtering fraction of 100% in sector 36d, encompassing the first illumination path 47. In between these extremes, two further sectors 36b and 36c are arranged, encompassing a third 49 and fourth illumination path 50. In the sector 36b, the filtering fraction is about 25%, i.e. about 25% of light having the wavelength of the excitation bands Ex. 1, Ex. 2 is filtered by the band-stop filtering material embedded in the substrate. In sector 36c, the filtering fraction is about 75%, meaning that only 25% light having the wavelength of the fluorescence excitation bands Ex.1 and Ex. 2 may transmit the illumination filter 36 in its fourth illumination path 50.

Using the illumination filters 36 of the embodiment shown in FIG. 3, one may choose between four discreet filtering fractions to be applied for adjusting the intensity of the fluorescence excitation bands Ex. 1 and Ex. 2, thereby stepwise adjusting the intensity of the excitation light.

The illumination filter system 2 of the present invention may be used to adjust the intensity ratio of the excitation light and the white (or visible) light, for example using an illumination filter system 2 according to a second embodiment. The design and function of the illumination filter system 2 of the second embodiment is explained with reference to FIGS. 4 and 5 in the following.

The design and function of another embodiment of an illumination filter system 2 will be explained with reference to FIGS. 4 and 5. The embodiment of the illumination filter system 2 shown in FIGS. 4 and 5 comprises the first optical filter 35, which may be a dual-notch filter to eliminate any light at the fluorescence emission bands Em.1, ppIX and Em.2, ICG. The illumination filter system 2 of the embodiment shown in FIGS. 4 and 5 furthermore comprises a (first) illumination filter as a second optical filter 36 adapted to attenuate light of the fluorescence excitation bands Ex.1, ppIX and Ex.2, ICG. The second optical filter 36 is configured to be moved from a first operation position 37, in which its first illumination path 47 is in optical communication with the light source 4 and the first optical filter 35, to a second operation position 38, in which its second illumination path 48 is in optical communication with the light source 4. Transition 39 between the first operation position 37 and the second operation position 38 is achieved by moving the second optical filter 36 along an axis of movement 40.

The second optical filter 36 may comprise a rectangular substrate in the shown embodiment a glass slide, 41 and the axis of movement 40 corresponds to the longitudinal direction L of the substrate 41.

A band-stop filter coating 42 is applied in a spatial pattern 43 of the substrate 41, which pattern 43 will be described in more detail below.

The illumination filter system 2 of the embodiment shown in FIGS. 4 and 5 furthermore comprises another (second) illumination filter 44 as a third optical filter 44 adapted to transmit light of the fluorescence excitation bands Ex.1, ppIX and Ex.2, ICG only. The second illumination filter (i.e. the third optical filter) 44 may be a band-pass filter 44. Like the second optical filter 36, the third optical filter 44 is configured to be moved from a first operation position 37, in which the first illumination path 47 of the third optical filter 44 is in optical communication with the light source 4, to a second operation position 38 in which the third optical filter 44 is in optical communication with the first optical filter 35 and the light source 4.

The third optical filter 44 is likewise comprised in a substrate 45, similar to the substrate 41, which is also composed of a clean glass slide having a rectangular shape, and which can be moved along its longitudinal axis L, which is identical to the axis of movement 40, during transition 39 from the first operation position 37 into the second operation position 38.

The substrate 45 of the third optical filter 44 comprises a band-pass filter coating 46 which is applied in a spatial band-pass filter pattern 43b similar to the spatial band stop filter pattern 43a of the second optical filter 36 on the substrate 41.

The spatial pattern 43 allows gradual attenuation of the intensity of fluorescence excitation bands Ex.1, ppIX and Ex.2, ICG from 100% to 0% by means of the second optical filter 36 as well as the intensity of the white light from 0 to 100% transmittance by means of the third optical filter 44.

Filters 36 and 44 are variable filters allowing adjustment of transmittance of the fluorescence excitation bands and the white light intensity, respectively, depending on their position in the path of illumination light 5 along the longitudinal direction L/the axis of movement 40. This is achieved by the spatial pattern 43 of coating 42, 46 which is identical in the shown in embodiment for both, the second optical filter 36 and the third optical filter 44.

The spatial pattern 43 masks a filtering fraction of 100%, e.g. has coverage of 100% of a first illumination path 47. Coverage here means the ratio of coated areas with respect to the total area of an illumination path which corresponds to the area of light passing through the respective filters 44, 36 of the illumination filter system 2.

The spatial pattern 43 has coverage of less than 100% of a second illumination path 48 on the substrate 41, 45. In the shown embodiment, the filtering fraction masks 0% in the exemplary second illumination path 48 meaning that no coating 46 at all is applied to the substrate 41, 45 on the position corresponding to the second illumination path 48. In between the first illumination path 47, which is on one end of substrate 41, 45 and the second illumination path 48, which is on the opposite end along the axis 40, i.e. longitudinal direction L of the substrate 41, 45, a plurality of illumination paths are provided from which as an example, two further illumination paths 49 and 50 are shown in FIGS. 5B and 5C.

The plurality of illumination paths 48, 49, 50, 47 are arranged along the axis of movement 40 on the substrate 41, 45. The spatial pattern 43 comprises a plurality of coating patches 51. In the shown embodiment, the coating patches 51 are coating squares 52. The center 53 of adjacent patches 51/squares 52 are spaced apart equidistantly, i.e. at the same distance d from one another. However, the area A of the patches 51 varies along the axis of movement 40. In the shown example, the length l of the patches 51, corresponds to the diagonal length l of the coating squares 52 that varies along the axis of movement 40. In detail, i.e. the diagonal of the coating squares 52 increases gradually from an area adjacent to the second illumination path 48 having no coating in direction along the axis of movement 40 to the first illumination path 47 having complete, i.e. 100% coating. The spatial pattern 43 starts from a filtering fraction of 100% spatial coverage in the first illumination path 47 shown on the left in FIG. 5, and the filtering fraction/coverage drops gradually along the axis of movement 40 until it is completely absent in the second illumination path 48 on the opposite side, the right side shown in FIG. 5.

The coverage, i.e. the ratio of coated versus total area of an illumination path determines the percentage of transmittance of the fluorescence excitation bands in case of a second band-stop filter 36 as well as the transmittance and thus intensity of the white light having a wavelength of about 400-750 nm in the shown embodiment by the band-pass filter 44. This can be seen for the four exemplary illumination path 47 to 50 in FIGS. 5A and 5D.

The intensities of the fluorescence excitation bands as well as the white light potion in the spectrally-modified illumination light 7 can thus be individually adjusted. The combination of all three filters results in a spectrum of the spectrally-modified illumination light 7 with the desired ratio between white light and excitation intensities as it is shown for one example in FIG. 4B. FIG. 4B shows, from left to right, the quenching of the fluorescence emission bands by the dual-notch filter 35, the attenuation of the white light portion by the band-pass filter 44, the attenuation of the fluorescence excitation light by the second band-stop filter 36. All three of these filters are in optic communication and result in the spectrally-modified illumination light 7 shown on the right side of FIG. 4B.

In order to obtain a nearly gradual changing coverage of the coating 42, 46, the distance d between the centers 53 of the coating patches 51/coating squares 52 should be significantly shorter than the diameter 54 of an illumination path. This way, filtering becomes more homogeneous. Significantly shorter in this respect means a magnitude of at least 10.

Figures 6A, 6B:
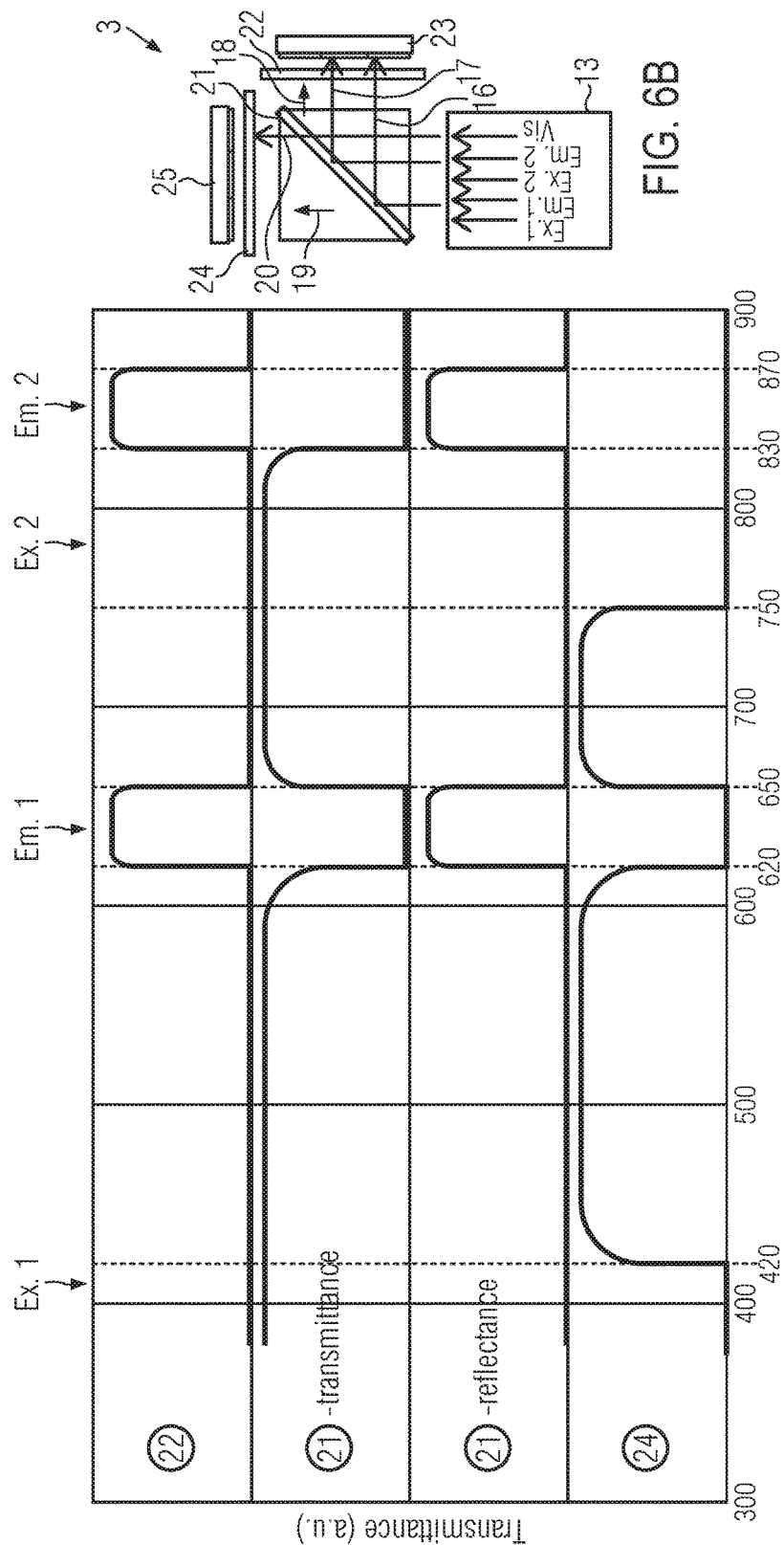
FIG. 6A shows the spectral characteristics (transmittance and reflectance) of filters and the beam splitter of the observation system of FIG. 1.
FIG. 6B shows an observation system comprising filters and a beam splitter having the spectra characteristics shown in FIG. 6A.

An exemplary embodiment of an observation system 3 is explained with reference to FIG. 6. FIG. 6B shows a schematic design of the observation system 3 and FIG. 6A shows the spectral characteristic (transmittance and reflection) of the components of the observation system 3.

The observation system 3 comprises a beam splitter 21 adapted to split the light image 13 of the illuminated object 6 into a first light portion 16, 17 along a first light path 18 and into a second light portion 20 along a second light path 19. The first light portion 16, 17 comprises the fluorescence emission bands Em.1 of ppIX and Em.2 of ICG. The second portion 20 comprises reflected visible light. In the shown embodiment, the beam splitter 21 is a polychroic mirror 55 that reflects light having a wavelength in the fluorescence emission bands Em.1 and Em.2 and transmits all light of the visible spectrum, except for the fluorescence emission band Em.1 falling into the white light spectrum. The observation system 3 furthermore comprises the two filters 22 and 24 as well as the two senses 23 and 25 already explained with respect to FIG. 1 above.

Further, filter 22, through which the first light portion 16, 17 passes before reaching the sensor 23, may be a band-pass filter adapted to transmit light of fluorescence emission bands Em.1 and Em.2 only. The filter 24, through which the second light portion 20 passes before reaching a sensor 25 may be a band-stop filter adapted to quench light of fluorescence emission bands Em.1, Em.2 as well as the fluorescence excitation bands Ex.1, Ex. 2.

Finally, FIG. 7 shows a further embodiment of an illumination filter 36. The illumination filter 36 of FIG. 7 has a disc-shape substrate 41. Said substrate 41 may be rotated about its center C along its axis of movement 40, which is a rotational movement indicated by the arrow. A series of eight windows 56a-56h is arranged along the axis of movement 40 in the disc-shaped substrate 41. Each window 56a-56h defines an different illumination path of the illumination filter 36 of the embodiment shown in FIG. 7. Each window 56a-56h is coated with a different band-stop filter coating 42, the different band-stop filter coatings 42 differing in the concentration of the band-pass filter material included therein, this way providing different filtering fractions for each window 56a-56h.

| REFERENCE NUMERALS | |
|---|---|
| 1 | Microscope/Medical Imaging Apparatus |
| 2 | Illumination Filter System |
| 3 | Observation System |
| 4 | Light Source |
| 5 | Illumination Light |
| 6 | Object |
| 7 | Spectrally Modified Illumination Light |
| 8 | Controller |
| 9 | Signal Line |
| 10 | Signal Line |
| 11 | Signal Line |
| 12 | Controller Interface |
| 13 | Light Image |
| 14 | Microscope Settings |
| 15 | Signal Line |
| 16, 16' | $1^{st}$ Light Portion |
| 17, 17' | $1^{st}$ Light Portion |
| 18 | $1^{st}$ Light Path |
| 19 | $2^{nd}$ Light Path |
| 20 | $2^{nd}$ Light Portion/VISR |
| 21 | Beam Splitter |
| 22 | Band-Pass Filter |
| 23 | $1^{st}$ Sensor/FL-Sensor |
| 24 | Band-Stop Filter |
| 25 | $2^{nd}$ Sensor/VISR-Sensor |
| 26 | Signal Line |
| 27 | Signal Line |
| 28 | Processing Unit |
| 29 | Signal Line |
| 30 | Signal Line |
| 31 | Signal Line |
| 32 | Signal Line |
| 33 | Display Device |
| 34 | Signal Line |
| 35 | Blocking (Band-stop) Filter |
| 36 | $1^{st}$ Illumination Filter/$2^{nd}$ Optical (Band-stop) Filter |
| 36a-36d | Sector |
| 37 | $1^{st}$ Operation Position |
| 38 | $2^{nd}$ Operation Position |
| 39 | Transition |
| 40 | Axis of Movement |
| 41 | Substrate |
| 42 | Band-Stop Filter Coating |
| 43 | Spatial Pattern |
| 43a | Band-stop filter pattern |
| 43b | Band-pass filter pattern |
| 44 | $2^{nd}$ Illumination Filter/$3^{rd}$ optical (Band-pass) filter |
| 45 | Substrate |
| 46 | Band-Pass Filter Coating |
| 47 | $1^{st}$ Illumination Path |
| 48 | $2^{nd}$ Illumination Path |
| 49 | $3^{rd}$ Illumination Path |
| 50 | $4^{th}$ Illumination Path |
| 51 | Filter Patch/Coating Patch |
| 52 | Coating Square |
| 53 | Center of Patch/Square |
| 54 | Diameter of Illumination Path |
| 55 | Polychroic Mirror |
| 56a-56h | Window |
| A | Area of Coating Patch/Square |
| d | Distance Between Adjacent Centers |
| C | Center |
| Ex. 1 | Excitation Band of ppIX |
| Em. 1 | Emission Band of ppIX |
| Ex. 2 | Excitation Band of ICG |
| Em. 2 | Emission Band of ICG |
| $I_1$ | Image Readout (FL) |
| $I_2$ | Image Readout (VISR) |
| L | Longitudinal Direction |
| I | Length of Patch/Diagonal of Square |
| P | Pseudo-image |
| VISR | Visible Reflected Light |

What is claimed is:

1. An illumination filter (36, 44) for an illumination filter system (2) for medical imaging (1), in particular multispectral fluorescence imaging, comprising a spatial filter pattern (43) masking a defined filtering fraction of a first illumination path (47) on the filter and masking a defined filtering fraction of a second illumination path (48, 49, 50) on the filter, wherein the filtering fraction of the first and the second illumination paths (47, 48, 49, 50) are different, wherein the spatial filter pattern (43) comprises a plurality of filter patches (51), and wherein respective centers (53) of adjacent filter patches (51) are essentially spaced equidistantly and respective areas (A) of the filter patches (51) vary.

2. The illumination filter (36, 44) of claim 1, wherein a filter coating (42) is applied as the spatial filter pattern (43) on a substrate (41), said coating (42) defining the filtering fraction of the first and the second illumination paths (47, 48, 49, 50) on the substrate (41).

3. The illumination filter (36, 44) of claim 2, wherein the spatial filter pattern (43) is a band-stop filter pattern (43a) or a band-pass filter pattern (43b).

4. The illumination filter (36, 44) of claim 3, wherein a band-stop filter coating (42) or a band-pass filter coating (46) is applied as the spatial filter pattern (43) on the substrate (41).

5. The illumination filter (36, 44) of claim 1, wherein the spatial filter pattern (43) extends over a plurality of illumination paths (47-50) and the filtering fraction is different in each illumination path (47-50).

6. The illumination filter (36, 44) of claim 5, wherein the plurality of illumination paths (47-50) is arranged along an axis of the illumination filter (36, 44).

7. An illumination filter (36, 44) for an illumination filter system (2) for medical imaging (1), in particular multispectral fluorescence imaging, comprising a spatial filter pattern (43) masking a defined filtering fraction of a first illumination path (47) on the filter and masking a defined filtering fraction of a second illumination path (48, 49, 50) on the filter, wherein the filtering fraction of the first and the second illumination paths (47, 48, 49, 50) are different, wherein the spatial filter pattern (43) comprises a plurality of filter patches (51), and wherein the filter patches (51) are filter squares (52).

8. The illumination filter (36, 44) of claim 7, wherein respective diagonal lengths (1) of the filter squares (52) varies in different illumination paths (47-50).

9. The illumination filter (36, 44) of claim 8, wherein the diagonal length (1) of the filter squares (52) varies along an axis of the illumination filter (36, 44).

10. An illumination filter system (2) for a microscope (1), in particular a multispectral fluorescence microscope, comprising an illumination filter (36, 44) having a spatial filter pattern (43) masking a defined filtering fraction of a first illumination path (47) on the filter and masking a defined filtering fraction of a second illumination path (48, 49, 50) on the filter, wherein the filtering fraction of the first and the second illumination paths (47, 48, 49, 50) are different, wherein the spatial filter pattern (43) comprises a plurality of filter patches (51), and wherein respective centers (53) of adjacent filter patches (51) are essentially spaced equidistantly and respective areas (A) of the filter patches (51) vary.

11. The illumination filter system (2) of claim 10, wherein the illumination filter (36, 44) is configured to be moved from a first operation position (37), in which the first illumination path (47) is in optical communication with a light source (4), to a second operation position (38), in which the second illumination path (48-50) is in optical communication with a light source (4).

12. The illumination filter system (2) of claim 10, comprising a first illumination filter (36) having a spatial band-stop filter pattern (43a) and a second illumination filter (44) having a spatial band-pass filter pattern (43b), wherein each of the first and second illumination filters (36, 44) is configured to be moved from a first operation position (37), in which the first illumination path (47) is in optical communication with a light source (4), to a second operation position (38), in which the second illumination path (48-50) is in optical communication with a light source (4).

13. The illumination filter system (2) of claim 10, further comprising a blocking filter (35) adapted to quench light of a fluorescence emission band (Em.1, Em.2).

14. An illumination filter system (2) for a microscope (1), in particular a multispectral fluorescence microscope, comprising an illumination filter (36, 44) having a spatial filter pattern (43) masking a defined filtering fraction of a first illumination path (47) on the filter and masking a defined filtering fraction of a second illumination path (48, 49, 50) on the filter, wherein the filtering fraction of the first and the second illumination paths (47, 48, 49, 50) are different, wherein the spatial filter pattern (43) comprises a plurality of filter patches (51), and wherein the filter patches (51) are filter squares (52).

* * * * *